United States Patent [19]

Murray et al.

[11] Patent Number: 5,412,116
[45] Date of Patent: May 2, 1995

[54] OXIDATION OF GLYCOSIDE SUBSTITUTED TAXANES TO TAXOL OR TAXOL PRECURSORS AND NEW TAXANE COMPOUNDS FORMED AS INTERMEDIATES

[75] Inventors: Christopher K. Murray; Jeffrey T. Beckvermit; David T. Bailey, all of Boulder; S. Kent Peterson, Denver, all of Colo.

[73] Assignee: Hauser Chemical Research, Inc., Boulder, Colo.

[21] Appl. No.: 133,449

[22] Filed: Oct. 7, 1993

Related U.S. Application Data

[63] Continuation-in-part of Ser. No. 973,076, Nov. 6, 1992, abandoned.

[51] Int. Cl.⁶ ............................................. C07D 305/14
[52] U.S. Cl. ..................................... 549/379; 549/414; 549/510
[58] Field of Search ........................ 549/414, 510, 399

[56] References Cited

U.S. PATENT DOCUMENTS 4,924,011  5/1990  Denis et al. ........................ 549/510
5,200,534  4/1993  Rao .................................... 549/510

Primary Examiner—Johann Richter
Assistant Examiner—John Peabody

[57] ABSTRACT

A process for the conversion of glycoside substituted taxanes to taxol and related compounds that can serve as precursors to taxol. The process includes the oxidation of glycoside substituted taxanes to convert the glycoside to the hydroxyl group. The oxidation can occur in the presence of an acid or followed by treatment with acid. Application of the process to 7-xylosyl taxol ("XT") yields taxol; application to other glycoside substituted taxanes forms compounds that can serve as precursors for taxol. The process includes the formation of certain new taxol related intermediate compounds having a hemialdal at the C-7 site on the taxane ring, which hemialdal can then be converted to taxol or taxol precursors. Since glycoside substituted taxanes are isolated with taxol from naturally occurring biomass, their conversion to taxol using the process of the present invention significantly improves the total yield of taxol from natural sources.

6 Claims, No Drawings

OXIDATION OF GLYCOSIDE SUBSTITUTED TAXANES TO TAXOL OR TAXOL PRECURSORS AND NEW TAXANE COMPOUNDS FORMED AS INTERMEDIATES

This application is a continuation-in-part of patent application Ser. No. 973,076, filed by Murray, et al. on Nov. 6, 1992, now abandoned.

BACKGROUND OF THE INVENTION

This invention relates generally to the field of preparing taxol and taxol precursors. The process of this invention also produces new taxane intermediate compounds.

Taxol, a material occurring in nature, and extracted from *Taxus brevifolia* (i.e., the Pacific yew tree) and other biomass has been identified as having significant tubulin binding (Schiff, P. B., et al., "Promotion of Microtubule Assembly in vitro by Taxol," *Nature*, 277: 665–67 (Feb. 1979)) and, when delivered to the cell, cytotoxicological activity which has been demonstrated through Phase III clinical trials. Taxol has now been approved for treatment of refractory ovarian cancer by the U.S. Food and Drug Administration. Generally, taxol is only isolated on a large scale from the bark of *Taxus brevifolia*; unfortunately, the yield is relatively low even by the most efficient processes. The actual and potential demand for taxol far exceeds the supply currently available by extraction of taxol from natural sources. (Kingston, "The Chemistry of Taxol, *Pharmac. Ther.*, Vol. 52, pp. 1–34, 5–6 (1991); "Kingston"). The process described herein could significantly increase the yield of taxol from these sources.

Taxol is a complex compound represented by the following formula:

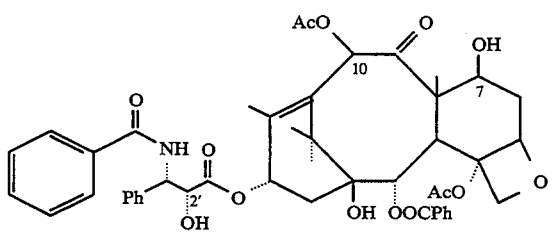

wherein reference numerals 2', 7 and 10 identify positions on the taxane ring significant to the nomenclature used herein.

Because of the physical and chemical complexity of the taxol molecule, the synthesis of taxol is extraordinarily difficult and has not been accomplished to date. "[I]t is . . . quite unlikely that a commercially feasible synthetic route to taxol will be developed before the end of this century." (Kingston at p. 24.) "Despite the progress made in [synthesizing taxol], the final total synthesis of taxol is, nevertheless, likely to be a multi-step, tedious, and costly process." (U.S. Pat. No. 5,015,744 at col. 1, lines 59 et seq.) The complexities of synthesizing taxol are evident from a cursory reading of Swindell, C. S. "Taxane diterpene synthesis strategies: A review." *Org. Prep, Proced. Int.* 23:465–543, 537 (1991) ("Swindell").

Even the partial synthesis of taxol from related compounds is quite difficult. "Taxol is the most functionally and stereochemically complex of the taxanes." (Swindell, at 467.) Among other things, the taxol molecule presents numerous reaction sites with similar chemical constituents in close proximity. This presents a problem, for example, with respect to any reaction attempting to affect any of the numerous oxygen substituents present at positions 1, 2, 4, 5, 7, 9 and 10 of the taxaneoring. (See, e.g., U.S. Pat. No. 4,876,399 to Holton et al., col. 3, lines 13–18.) This chemical complexity makes it difficult to direct reactions with significant specificity, except through the use of blocking agents and very controlled reaction parameters which favor a particular reaction at a particular site. Accordingly, yields of the desired product from reaction of taxol or taxol related compounds with a given reagent are frequently quite low.

In addition, the stereochemistry of the taxol molecule is considerably more complex than even the two dimensional formula depicted above. In fact, the taxol molecule has been characterized as "an inverted cup shape, in which the ester side chain lies across the opening of the cup." (Kingston at 3.) Kingston includes a more detailed two-dimensional depiction of taxol's stereochemistry.

As a result of these considerations, the chemistry of taxol and taxol related compounds is difficult and unpredictable.

Researchers have attempted to avoid some of these problems by focusing on the possibility of developing taxol related materials with tubulin binding and cytotoxicological activity. However, "with few exceptions, changes in the taxane skeleton appear to reduce the activity of taxol." (Kingston at 31.) Thus, the production of taxol is still generally preferred over other compounds with similar or analogous structures.

The current invention relates specifically to the partial synthesis of taxol and taxol precursors from taxanes containing a glycoside group at the C-7 position. (See the structural drawing above.) These glycoside taxanes are produced in nature and can be recovered with taxol during production from *Taxus brevifolia*. Glycoside substituted taxanes such as 10-deacetyl-7-xylosyl taxol (i.e., "10-DAXT") have been isolated along with taxol (see V. Senilh, et al., "New Derivatives of Taxol, . "*J Nat Prod.* 47:131 (1984); "Senilh et al."). The naturally-occurring 7-glycoside taxanes include the following specific materials: 7-xylosyl-10-deacetyl taxol A, 7-xylosyl-10-deacetyl taxol B, 7-xylosyl-10-deacetyl taxol C, 7-xylosyl-taxol A, 7-xylosyl taxol B, and 7-xylosyl taxol C. The structure of these compounds is represented by the following examples:

10-deacetyl-7-xylosyl taxol A:

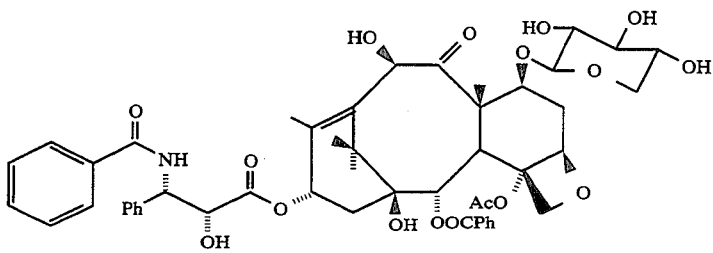

10-deacetyl-7-xylosyl taxol B:

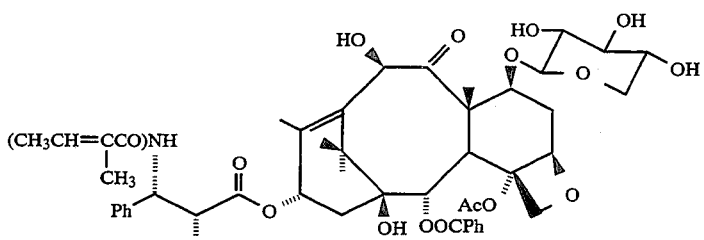

and 10-deacetyl-7-xylosyl taxol C:

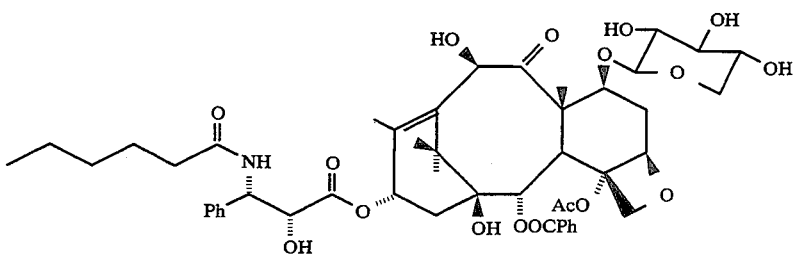

In addition, the process of this invention may be applied to 10-deacetyl-7-xylosyl baccatin III ("10-DAXB"):

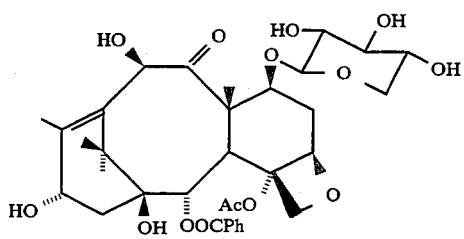

Unless otherwise utilized herein, "taxol" shall collectively refer to the A, B and C variants. "Taxane" is utilized herein to refer to any compound having the characteristic cyclic structure repeated in the foregoing diagrams.

Typically, acid hydrolysis is used to remove, i.e., cleave, glycosides from chemical compounds to which they are attached. Common hydrolyzing agents include acetic or mineral acids in water/MeOH. Accordingly, hydrolysis of glycoside substituted taxanes has been suggested in the literature. (See Senilh et al. at 137.) However, replication of the experiment shown in Senilh et al. utilizing methanol and acetic acid as the hydrolyzing agent with 10-DAXT confirmed the decomposition of the taxane into numerous molecular fragments. The production of 10-DAT, i.e., the discrete cleavage of the glycoside from the taxane molecule, could not be observed. This indicates that the reaction shown in Senilh et al. is not selective and is consistent with the general observation that the taxol molecule is sensitive to strongly acidic hydrolysis conditions. (Kingston at 15, Section 3.6.)

It has not been previously known that it was possible to use taxanes containing a glycoside group at the C-7 position for the synthesis of taxol or taxol precursors. To date all partial synthetic routes for the production of taxol have derived from baccatin III, a significantly different starting material. (Kingston at 17.) Since baccatin III is not directly recovered from biomass, there are preliminary conversion steps to generate it as a "starting material."

SUMMARY OF THE INVENTION

We have now discovered a simple, efficient and surprisingly selective process for converting the xylose substituted taxanes to taxol or taxol precursors, such as 10-deacetyl taxol (i.e., "10-DAT"). The method described herein includes selective oxidation of glycoside substituted taxanes using oxidizing agents, such as periodic acid or salts thereof. The oxidation may also be conducted in the presence of an acid or followed by acid hydrolysis, if necessary.

Glycoside substituted taxanes may be recovered from natural biomass in amounts exceeding that of taxol. (Abstract O-12 from the International Research Congress of Natural Products, Jul. 21–26, 1991, "The Bark of *Taxus brevifolia* Contains Much More Realizable Taxol than is Currently Accepted," Koppaka V. Rao: College of Pharmacy, University of Florida, Gainesville, FLa. 32610). Accordingly, the use of the present invention can more than double the amount of taxol ultimately recovered from *Taxus brevifolia* or other biomass sources.

It is an object of this invention to provide a simple and efficient method for the production of taxol or taxol precursors from glycoside substituted taxanes.

It is a further object of this invention to produce certain new taxane compounds that can be utilized to produce taxol or precursors to taxol.

DESCRIPTION OF THE INVENTION AND THE PREFERRED EMBODIMENT

We have now discovered a process for the oxidative cleavage of glycoside substituted taxanes. The process is mild, selective and efficient.

The oxidation reactions of this invention are mild enough that their progress can be monitored, and they do not continue beyond the desired end-point to produce unwanted products. Generally the reactions can be monitored utilizing high-pressure liquid chromatography ("HPLC") and thin-layer chromatography ("TLC"). When the presence of either glycoside substituted taxane starting material or oxidation intermediate is no longer detected, the reaction is deemed to be complete.

In addition, the oxidation is quite selective. This is true in two respects. First, the oxidation occurs selectively to cleave the glycosides on the C-7 site. Normally, one should anticipate that the introduction of an oxidizing agent to a glycoside substituted taxane would cause oxidation at sites other than C-7 on the taxane ring, such as the 2'-hydroxy and the 10-position on 10-DAXT. In fact, oxidation does not appear to occur at these positions. Secondly, the introduction of an oxidizing agent to mixtures containing glycoside substituted taxanes and other non-glycoside substituted taxane compounds does not result in oxidation of the other taxanes. Such mixtures occur in biomass or partial separations or extracts of such biomass. This selectivity enables the oxidative cleavage of the glycosides to be conducted at various stages during the isolation of taxol from *Taxus brevifolia* or other naturally-occurring materials.

Finally, the oxidation reaction is efficient. It has been possible to obtain complete cleavage of the glycosides from the taxane molecules to which they are attached. The reactions provide relatively high yields of taxol or taxol precursors depending on the amount of taxane starting material and the procedures employed in the isolation and purification of the reaction products.

The method of the current invention can be utilized with various glycoside containing taxane starting materials. Although the only naturally occurring glycoside substituted compounds identified to date are the xylose substituted taxanes in the C-7 position (i.e., compounds 3-8 in Senilh et al.), there is no reason that the same oxidative cleavage reactions would not occur with other glycosides substituted at the C-7 position or elsewhere on the taxane molecule.

Oxidation can be performed on the glycoside substituted taxanes after their isolation or on mixtures containing the glycoside substituted taxanes. Thus, it is not necessary to separate the glycoside substituted taxanes from other taxanes recovered from biomass before they are oxidized in accordance with this invention.

The cleavage of the glycoside side chain is accomplished by using an effective oxidizing amount of an oxidizing agent. Effective oxidizing agents include, but are not limited to, those listed in Table I.

TABLE I

| (Oxidizing Agents) | |
|---|---|
| periodic acid and salts thereof, such as, potassium or sodium periodate | $HIO_4$, $KIO_4$, $NaIO_4$ |
| lead tetraacetate | $Pb(OAc)_4$ |
| sodium bismuthate | $NaBiO_3$ |
| tetrabutylammonium periodate | $Bu_4NIO_4$ |
| manganese dioxide | activated $MnO_2$ |
| pyridinium chlorochromate | PCC |
| potassium permanganate | $KMnO_4$ |

An effective amount of one or more oxidizing agents can be utilized. In particular, one or more oxidizing agents from the above list can be employed. Although periodic acid and its salts are the preferred oxidizing agents and are listed first, Table I does not purport to rank the materials, other than periodic acid and its salts, according to their effectiveness in performing the oxidation step. The relative effectiveness of the various possible oxidizing agents depends upon the concentration employed and other conditions of the reaction.

Various amounts of the oxidizing agent can be employed, but generally it should be present in the range of 1-10 molar equivalents of oxidizing agent per mole of glycoside. Preferably, at least 2 equivalents of oxidizing agent per molar equivalent of glycoside is needed for the reaction to proceed to completion.

To facilitate mixing of the starting materials, the oxidation is preferably accomplished utilizing an effective dissolution amount of a taxane solvent which is compatible with the particular oxidizing agent or agents employed. Typical solvents include tetrahydrofuran, water, acetone, aqueous dioxane, or mixtures thereof or other taxane solvents known to one of ordinary skill in the art.

In a preferred embodiment of the invention the oxidative cleavage of the glycoside functional groups on taxanes is accomplished by dissolving the taxane using tetrahydrofuran, water, acetone, or mixtures thereof as the solvent, and utilizing periodic acid or salts thereof as the oxidizing agent. The xylose group is oxidized in two to twenty-four hours for solutions which are approximately 0.1 mg./ml. of taxane using 2-10 molar equivalents of the periodate reagent.

The oxidation can be enhanced by performing it in the presence of acid or followed by hydrolysis with an acid. Acids which can be used for this purpose include acetic acid (including glacial acetic acid or aqueous acetic acid) and mineral acids. Acetic acid is preferred and can be used in aqueous form as all or part of the solvent during the oxidation step.

The oxidation process of the present invention has revealed the existence of novel taxane compounds having the general formula:

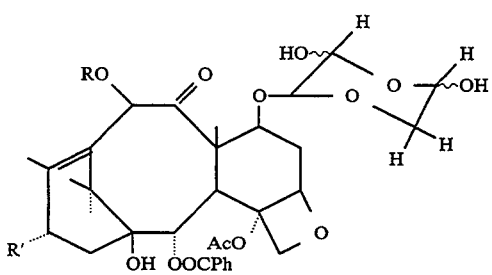

Wherein R represents Ac or H and R' represents:

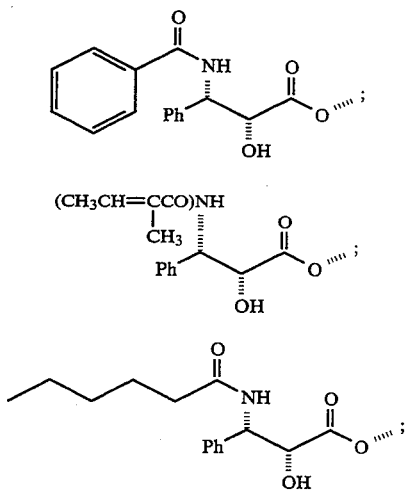

the hydroxyl group or any other organic side chain except a glycoside, diol or another constituent that would be oxidized in preference to the glycoside on the taxane ring, e.g. the C-7 site. For lack of a better term, we have chosen to designate these compounds as the "oxo" form of the xylosyl compounds from which they were obtained by oxidation.

The intermediate compounds shown above are in equilibrium with homologs of the side chain at the C-7 site. These include hemialdals in open (i.e., non-cyclic) form. However, the equilibrium constant is such that the structure shown in the immediately preceding diagram is greatly preferred. As used herein, the structure shown above is intended to include the homologs of the C-7 hemialdal side chain in equilibrium with it.

Because the intermediate compound is an equilibrium of several homologs, it is difficult to confirm its existence through the use of direct NMR analysis. The existence of these new intermediate compounds, however, was confirmed by chemical reduction of the intermediate with sodium cyanoborohydride. This is a common chemical conversion method for hemialdal-type structures. When the product of such a reduction is found to be:

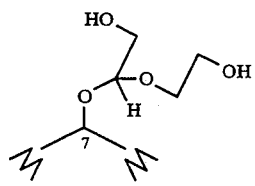

it can be reliably deduced that the original side chain was:

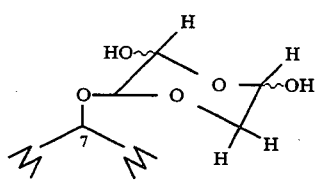

The method used for identifying the intermediates is shown in more detail in Example 7. Based on this chemical conversion and NMR analysis of the intermediate, the intermediate compounds are clearly hemialdals.

The reduced oxidation intermediates are also novel compounds that can be converted to taxol or taxol precursors as illustrated in Example 8.

These hemialdal compounds represent the intermediates in the conversion of the side chain at the C-7 site from the glycoside to the hydroxyl. That "conversion" occurs through oxidation to the intermediate side-chain, cleavage of the side chain, and replacement with the hydroxyl group. The entire conversion to the hydroxyl group may occur during oxidation, if sufficient molar concentrations of oxidizing agent are present, or may be effected through use of a hydrolyzing agent, as discussed previously. The hydrolyzing agent can either be included with the oxidation reagent or can be utilized in a separate, subsequent step with sufficient hydrolyzing agent being present to complete the conversion from the glycoside to the hydroxyl group. The presence of oxidizing agent during hydrolysis appears to facilitate the conversion to the final product.

The process of the present invention can be used to produce taxol and precursors of taxol. Where the starting material utilized is 7-xylosyl taxol ("XT"), application of the process of this invention will produce taxol directly. Where the starting material is another C-7 glycoside substituted taxane, the resulting product will be the C-7 hydroxyl form of that taxane. These materials are precursors for and may be converted to taxol.

The novel process and compounds of our invention are illustrated by the following examples:

EXAMPLES

Materials and Methods: All solvents and reagents employed in the examples were used as received from the manufacturer. Xylosyl taxanes were isolated from the bark of *Taxus brevifolia* in accordance with literature methods. Reactions were monitored by thin-layer chromatography ("TLC") using 0.25 mm. Whatman Silica Gel 60A K6F (glass support) or 0.25 mm. E. M. Industries Silica Gel 60 (aluminum support) silica gel plates. Reactions were also monitored by high-pressure liquid chromatography ("HPLC") using a system consisting of a model L-6200 pump, Model AS-4000 or L-3000 UV/VIS/DAD detector (Hitachi Instruments, Inc.). The system was equipped with an NEC 286 computer with 40M hard drive and Lab Manager HPLC software (Hitachi Instruments, Inc.). HPLC columns used included a 4.6 mm.×250 mm. Phenyl column, packed with 5 μm diphenyl material (Supelco, Inc.); a 4.6 mm.×250 mm., 5 μm, 60 angstrom Pentafluorophenyl (PFP) column (ES Industries); and a 4.6 mm.×20 mm. phenyl guard column (Jones Chromatography). Silica Gel for flash chromatography (230 to 400 mesh) was supplied by Scientific Products. Yields refer to chromatographically and spectroscopically pure compounds unless otherwise noted. As used herein, "chrom purity" refers to the HPLC normalized peak area percentage at 227 nm for a given component. Melting points are uncorrected. $^1$H-NMR and $^{13}$C-NMR chemical shifts are reported in ppm. relative to tetramethylsilane using residual non-deuterated NMR solvent for reference. NMR data was obtained using a Bruker WP-270 MHz, Bruker ACE-300 MHz, Bruker AM-500 or a Varian Gemini 300 MHz NMR spectrometer. Mass spectra were measured at M-Scan Inc. using a VG Analytical ZAB 2-SE high field mass spectrometer, or a VG platform (API mass spectrometer)—electrospray mode.

EXAMPLE 1

This example demonstrates the conversion of 7-xylosyl taxol ("XT") to taxol using a single oxidation step.

A 142 mg. sample of XT was dissolved in acetic acid (0.88 ml.), water (0.221 ml.), and tetrahydrofuran (THF, 0.44 ml.). To this mixture was added 198 mg. of sodium periodate ($NaIO_4$). The mixture was heated to 50° C. for 6 days. The reaction was followed by TLC and HPLC until no more starting XT or intermediate remained. The crude reaction mixture was dissolved in ethyl acetate, the organic layer was washed with saturated sodium thiosulfate and brine, and then dried over anhydrous magnesium sulfate. After concentrating to a solid, the taxol was isolated by flash silica gel chromatography to yield 102 mg. of white solid. The melting point was low, so the white solid was crystallized from acetone/hexane. A white crystalline material was isolated (57.2 mg., 47% yield): m.p. 212°–215° C. (natural taxol, m.p. 214°–215° C.). FT-IR (solid) 3510 (m), 3440 (m), 2945 (w), 1736 (s), 1707 (s), 1647 (m), 1371 (m), 1275 (s), 1246 (s), 1176 (m), 1109 (m), 1074 (m), 985 (m), 710 (m) cm.$^{-1}$; $^1$H-NMR (300 MHz, $CD_2Cl_2$) 1.12 (s, 3H), 1.22 (s, 3H), 1.63 (s, 3H), 1.81 (m, 1H), 1.81 (s, 3H), 2.21 (s, 3H), 2.26 (dd, J=9.0, 15.2 Hz, 1H), 2.35 (m, 1H), 2.39 (s, 3H), 2.50 (ddd, J=6.7, 9.6, 14.7 Hz, 1H), 3.79 (d, J=7.1 Hz, 1H), 4.19 (d, J=8.3 Hz, 1H), 4.27 (d, J=8.3 Hz, 1H), 4.40 (dd, J=6.7, 11.0 Hz, 1H), 4.79 (d, J=2.7 Hz, 1H), 4.94 (dd, J=2.3, 9.6 Hz, 1H), 5.64 (d, J=7.1 Hz, 1H), 5.75 (dd, J=2.4, 8.3 Hz, 1H), 6.23 (qt, J=1.5, 9.0 Hz, 1H), 6.25 (s, 1H), 7.08 (d, J=8.8 Hz, 1H), 7.32–7.60 (m, 10H), 7.64 (tt, J =1.2, 7.6 Hz, 1H), 7.74 (dd, 1.5, 8.5 Hz, 2H), 8.14 (dd, J=1.5, 8.4 Hz, 2H); $^{13}$C-NMR (75 MHz, $CD_2Cl_2$) 9.77, 15.05, 21.00, 22.05, 22.92, 27.00, 36.06, 36.19, 43.55, 46.16, 55.61, 58.93, 72.60, 72.72, 73.78, 75.42, 76.00, 76.78, 79.46, 81.47, 84.70, 127.48, 127.49, 128.62, 129.05, 129.14, 129.33, 129.83, 130.61, 132.29, 133.58, 134.10, 134.33, 138.79, 142.59, 167.29, 167.47, 170.92, 171.74, 173.21, 204.17. The $^-$H- and $^{13}$C-NMR spectra of the synthetic taxol produced in this example were identical in all respects with those of the natural product. Mass spectrum (FAB, m-nitrobenzyl alcohol matrix) m/z 854 (M+H)$^+$, m/z 876 (M+Na)$^+$; (natural taxol m/z 854 (M+H)$^+$, m/z 876 (M+Na)$^+$).

EXAMPLE 2

This example illustrates the conversion of XT to Taxol.

A 244.7 mg sample of 7-xylosyltaxol (93% chrom purity, 0.248 mmoles) was dissolved in a 4:2:1 solution of acetic acid, tetrahydrofuran, and water (0.15M). Sodium periodate (371.6 mg, 1.74 mmoles, 5 cq) was added, and the reaction was heated to 60° C. (oil bath). After 4.5 days, HPLC analysis indicated taxol as the major product and no 7-xylosyltaxol or oxidation intermediates. The crude mixture was diluted with ethyl acetate and washed successively with sodium thiosulfate and brine solutions. The solution was dried over magnesium sulfate and concentrated to a solid.

Flash silica gel chromatography and selective precipitation were used to isolate the final product. An isocratic elution of 50% EtOAc/hexane was used. The appropriate fractions were combined and concentrated to a solid. The residue was then dissolved in 3 ml of acetone and transferred to 30 ml of hexane. Vacuum filtration yielded 129.1 mg of a white solid, which corresponded to taxol (92% chrom purity) by HPLC analysis. The overall yield for this conversion was 61%.

EXAMPLE 3

This example demonstrates the conversion of 10-deactyl-7-xylosyl taxol ("10-DAXT") to ("10-DAT") using a single oxidation step.

To 207 mg 10-DAXT (0.219 mmol, 92.5% chromatographic purity) partially dissolved in 519 μl THF, 259 μl $H_2O$, and 1040 μl AcOH was added 407 mg $NaIO_4$ (1.904 mmol). The mixture was then heated to 60° C. for 113 hours. The mixture was diluted with EtOAc and washed consecutively with $Na_2S_2O_4$, $H_2O$, brine, and then dried over $MgSO_4$. The evaporated residue was purified via flash chromatography (7% MeOH/$CH_2Cl_2$) giving 136 mg (76% yield at a chrom purity of 93.8%) of a white solid. Melting point after an acetone/hexane precipitation was 182°–183° C. The data matches the data for the 10-DAT product isolated in Example 4, and the data for natural 10-DAT.

EXAMPLE 4

This example illustrates the conversion of 10-deacetyl 7-xylosyl taxol ("10-DAXT") to 10-deacetyl taxol ("10-DAT") using a two-step method.

A 146 mg. sample of 10-DAXT was dissolved in 0.68 ml. of tetrahydrofuran (THF) followed by the sequential addition of 0.58 ml. water and 3.5 molar equivalents of sodium periodate ($NaIO_4$). The mixture was stirred at room temperature for four hours. The solvents were evaporated and the mixture containing oxo-10-DAT was redissolved in acetic acid (AcOH)/THF/$H_2O$ (4:2:1) to make a 0.065M mixture. This mixture was heated to 50° C. for 75.5 hours. The reaction was monitored by TLC and HPLC until no more oxidation intermediate remained. The mixture was dissolved in methylene chloride followed by filtration to remove the salts. The organic layer was washed with $H_2O$, saturated sodium thiosulfate, brine, and dried over anhydrous magnesium sulfate. The solid was purified by silica gel chromatography (5% MeOH/$CH_2Cl_2$) to give 86.1 mg. of 10-DAT (68.7% yield). The 10-DAT product was characterized by $^1$H-NMR, $^{13}$C-NMR, in comparison with natural material. Specifically, the final product was identified by the following analyses: FT-IR (solid) 3427 (b), 2939 (w), 1728 (s), 1660 (m), 1271 (s), 1246 (s), 1136 (m), 1109 (m), 1070 (m), 1026 (m), 985 (m), 710 (m) cm$^{-1}$; $^1$H-NMR (300 MHz, $CD_2Cl_2$) 1.08 (s, 3H), 1.17 (s, 3H), 1.71 (s, 3H), 1.79 (d, J=1.1 Hz, 3H), 1.79 (m, 1H), 2.23 (m, 1H), 2.38 (s, 3H), 2.53 (m, 1H), 3.87 (d, J=7.0 Hz, 2H), 4.16 (d, J=8.6 Hz, 1H), 4.22 (m, 1H), 4.28 (d, J=8.3 Hz, 1H), 4.78 (d, J=2.7 Hz, 1H), 4.93 (dd, J=2.0, 10.3 Hz, 1H), 5.18 (s, 1H), 5.64 (d, J=7.1 Hz, 1H), 5.75 (dd, J=2.8, 8.8 Hz, 1H), 6.18 (m, 1H), 7.19 (d, J=8.8 Hz, 1H), 7.32–7.55 (m, 9H), 7.64 (tt, J=2.3, 7.4 Hz, 1H), 7.75 (dd, J=1.5, 7.8 Hz, 2H), 8.12 (dd, J=1.5, 7.8 Hz, 2H); $^{13}$C-NMR (75 MHz, $CD_2Cl_2$) 10.08, 14.58, 20.83, 22.90, 26.77, 32.50, 37.33, 43.40, 46.92, 55.58, 58.02, 72.35, 72.71, 73.80, 74.86, 75.20, 76.88, 79.07, 81.44, 84.44, 127.42, 127.43, 128.50, 128.98, 129.08, 129.22, 129.75, 130.51, 132.22, 134.03, 134.24, 136.54, 138.51, 138.72, 167.14, 167.39, 170.94, 172.95, 211.65. The $^1$H- and $^{13}$C-NMC spectra of the synthetic 10-DAT produced in this example were identical to the natural product. Mass spectrum (FAB, m-nitro benzyl alcohol matrix) m/z 812 (M+H)$^+$, m/z 834 (M+Na)$^+$; (natural 10-DAT m/z 812 (M+H)$^+$, m/z 834 (M+Na)$^+$).

The following examples illustrate the efficacy of oxidizing agents other than periodate.

EXAMPLE 5

A 10 mg. sample of 10-DAXT was dissolved in 0.04 ml. glacial acetic acid followed by the addition of 2.5 molar equivalents of sodium bismuthate (NaBiO$_3$). The mixture was stirred at room temperature for 20 hours while monitoring by TLC. Phosphoric acid (3.33N, 0.017 ml.) was added followed by filtration to remove the salts, and evaporation. An aliquot of the product was analyzed by HPLC and TLC indicating 10-DAT was formed when compared to a standard of natural 10-DAT.

EXAMPLE 6

A 5 mg. sample of 10-DAXT was dissolved in 0.96 ml. of methylene chloride at room temperature followed by the addition of 3.5 mg. of pyridinium chlorochromate. The mixture was stirred for 5 days at room temperature while monitoring by TLC and HPLC. The crude mixture was analyzed by HPLC and shown to contain 10-DAT by comparison with a known standard.

EXAMPLE 7

This example illustrates the reduction of "oxo-10-DAXT" to the oxo-10-DAXT diol form.

A 724 mg sample of oxo-10-DAXT was dissolved in 55:45 THF/H$_2$O (0.18M solution) with a trace of methyl orange indicator. To this solution was added 196 mg of NaBH$_3$CN (4 eq) along with 1.7 ml of AcOH. The reaction proceeded at r.t. After 6.25 hours the reaction was not complete, so 49 mg of NaBH$_3$CN (1 eq) was added along with 0.5 ml of AcOH. After 23 hours the reaction was complete. The crude mixture was then diluted with EtOAc and washed successively with saturated NaHCO$_3$ solution, water, and brine. The solution was then dried over MgSO$_4$ and concentrated to give 685 mg of a white solid.

Flash silica gel chromatography yielded the final product. A 685 mg sample of the crude diol was eluted with a 7% MeOH/CH$_2$Cl$_2$ solution to give 579 mg of oxo-10-DAXT diol, at 96% chrom purity. The overall yield for this conversion was 81%. The product had a melting point of 175–178 deg. C. The following data confirmed the structure of the product as the reduced diol of the oxidation intermediate of 10-DAXT (oxo-10-DAXT):

FT-IR (solid) 3400 (m), 2950 (w), 1725 (s), 1525 (w), 1475 (w), 1425 (w), 1375 (w), 1300 (m), 1275 (s), 1225 (s), 1175 (m), 1050 (s), 1025 (m), 975 (m), 725 (m) cm$^{-1}$. $^1$H-NMR (270 MHz, CD$_2$Cl$_2$) 1.05 (s, 3H), 1.15 (S,3H),1.74 (s, 3H), 1.83 (s, 3H), 1.95 (m 1H), 2.15–2.30 (m, 2H), 2.36 (s, 3H), 2.70 (ddd, J=6.7, 9.7, 14.7 Hz), 1H), 2.95 (m, 2H), 3.3–3.6 (m, 4H), 3.62 (m, 2H), 3.85 (d, J=7.0 Hz, 1H), 4.13 (m, 3H), 4.25 (m, 2H), 4.48 (t, J=5.3 Hz, 1H), 4.79 (m, 1H), 4.91 (dd, J=2.3, 10.0 Hz, 1H), 5.19 (br s, 1H), 5.60 (d, J=7.0 Hz, 1H), 5.71 (dd, J=2.3, 8.8 Hz, 1H), 6.16 (dd, J=1.5, 8.8 Hz, 1H), 7.28–7.55 (m, 10H), 7.61 (tt, J=1.4, 7.6 Hz, 1H), 7.73 (dd, J=1.17, 7.6 Hz, 2H), 8.10 (dd, J=1.7, 7.63 Hz, 2H); $^{13}$C-NMR (67.5 MHz, CD$_2$Cl$_2$) 10.98, 14.61, 20.93, 22.91, 26.83, 35.72, 36.28, 43.47, 47.13, 55.70, 62.26, 68.32, 69.74, 72.65, 73.82, 75.13, 76.78, 79.10, 79.33, 81.29, 84.37, 104.49, 127.37, 127.46, 128.48, 128.98, 129.07, 129.20, 129.81, 130.53, 132.20, 134.01, 134.32, 136.53, 138.63, 138.79, 167.10, 167.53, 171.07, 173.13, 211.05. Mass spectrum (FAB, m-nitro benzyl alcohol matrix) m/z 938.4 (M+Na)$^+$).

EXAMPLE 8

This experiment demonstrated that the reduced oxidation intermediate can also be converted to taxol or taxol precursors.

A 4.8 mg. sample of 10-DAXT oxidized intermediate in diol form was dissolved in THF (0.022 ml.), water (0.011 ml.), and acetic acid (0.044 ml.). The mixture was then heated to 50° C. After one day, HPLC data indicated 10-DAT was formed by comparison with a standard of 10-DAT. The crude mixture was also "spiked" with an authentic sample of naturally occurring 10-DAT isolated from biomass and analyzed by HPLC. The data shows that the product formed from the reduced diol of the oxidation intermediate was 10-DAT.

The description and examples set forth herein are intended to illustrate representative embodiments of the invention. The claims which follow are not intended to be limited to the specific disclosed embodiments. The invention is susceptible to modification, variation and change without departing from the proper scope or fair meaning of the following claims.

We claim:

1. A compound useful for the production of taxol or precursors thereof comprising:

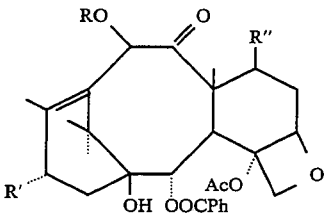

Wherein R represents Ac or H; R' represents:

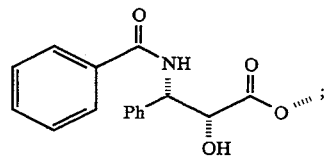

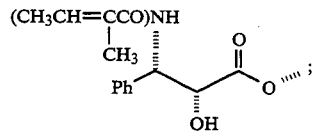

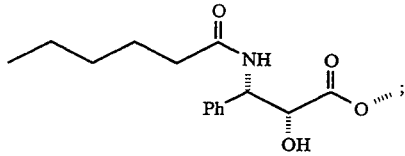

OH; and R" represents:

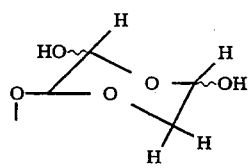
or
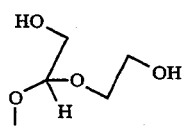
2. The compound of claim 1 in which R″ is:
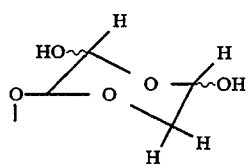
3. The compound of claim 2 wherein R′ is:
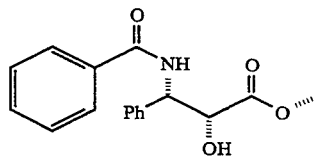
4. The compound of claim 2 wherein R′ is:
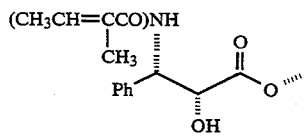
5. The compound of claim 2 wherein R′ is:
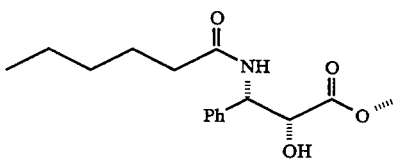
6. The compound of claim 2 wherein R′ is OH.
* * * * *